(12) United States Patent
Roney et al.

(10) Patent No.: US 8,433,773 B2
(45) Date of Patent: Apr. 30, 2013

(54) METHODS, SYSTEMS, AND COMPUTER PROGRAM PRODUCTS FOR PROVIDING INTELLIGENT MONITORING SERVICES

(75) Inventors: William N. Roney, Loganville, GA (US); Christopher P. Britton, Alpharetta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 606 days.

(21) Appl. No.: 12/641,740

(22) Filed: Dec. 18, 2009

(65) Prior Publication Data

US 2011/0154131 A1 Jun. 23, 2011

(51) Int. Cl.
*G06F 15/16* (2006.01)

(52) U.S. Cl.
USPC .......................................................... 709/217

(58) Field of Classification Search .................... 709/217
See application file for complete search history.

(56) References Cited

U.S. PATENT DOCUMENTS

| | | | |
|---|---|---|---|
| 5,978,737 A * | 11/1999 | Pawlowski et al. | 701/301 |
| 6,732,063 B2 * | 5/2004 | Famili et al. | 702/188 |
| 7,257,515 B2 * | 8/2007 | Haeuptle | 702/185 |
| 8,160,916 B2 * | 4/2012 | Moukas et al. | 705/7.29 |
| 2003/0149550 A1 * | 8/2003 | Famili et al. | 702/188 |
| 2008/0102453 A1 * | 5/2008 | Ghosh et al. | 435/6 |
| 2009/0234916 A1 * | 9/2009 | Cosentino et al. | 709/203 |
| 2009/0313204 A1 * | 12/2009 | Van Zon | 706/52 |
| 2010/0030576 A1 * | 2/2010 | Gregory | 705/3 |

* cited by examiner

*Primary Examiner* — Firmin Backer
*Assistant Examiner* — Jonathan Bui
(74) *Attorney, Agent, or Firm* — Cantor Colburn LLP

(57) ABSTRACT

Methods, systems, and computer program products for intelligent monitoring services are provided. A method includes sampling data for a subject over a defined time period and calculating a normative value for the defined time period based on the sampled data. The method also includes monitoring incoming data for the subject, comparing a monitored value for the incoming data to the normative value, and generating a responsive action when the monitored value deviates from the normative value.

17 Claims, 3 Drawing Sheets

METHODS, SYSTEMS, AND COMPUTER PROGRAM PRODUCTS FOR PROVIDING INTELLIGENT MONITORING SERVICES

BACKGROUND

The present invention relates generally to data monitoring systems and, more particularly, to methods, systems, and computer program products for providing intelligent monitoring services.

In current monitoring systems where a large number of metrics are monitored and the values stored persistently, a mechanism is needed to evaluate all of these metrics in real-time to alert to emerging changes from the normal behavior. Evaluating large amounts of data can be a daunting task, even when the data is graphically presented, as the quantity of the data represented in graphical form can overwhelm the reviewer of the data and important information may be visually "buried" in the graph.

One example application of monitoring large quantities of data includes, e.g., a system that measures transaction rates on a high volume of databases. Another application includes a system that measures heart rates for thousands of patients. Traditional monitoring methods use boundary alerting. Boundary alerting involves establishing pre-defined static values and using the pre-defined static values to establish a baseline of acceptable behavior. This may be implemented by defining alert rules specific to each metric after first determining what the norm is for the metric. Using the first example above, if the transaction rate exceeds 100 transactions per second (whereby the static value is 100), an alert may be generated. Using the second example above, if the heart rate goes higher than 120 beats per minute (bpm) or lower than 60 bpm (whereby the static value is represented by a maximum and minimum acceptable value), an alert may be generated. Boundary alerting oftentimes use artificially wide boundaries in order to prevent false alarms, which can result in a delayed alert.

What is needed, therefore, is way to efficiently monitor quantities of data and timely detect any anomalies.

BRIEF SUMMARY

The above-stated shortcomings and disadvantages are overcome or alleviated by methods, systems, and computer program products for providing intelligent monitoring services.

An exemplary method for providing intelligent monitoring services includes sampling data for a subject over a defined time period and calculating a normative value for the defined time period based on the sampled data. The method also includes monitoring incoming data for the subject, comparing a monitored value for the incoming data to the normative value, and generating a responsive action when the monitored value deviates from the normative value.

An exemplary system for providing intelligent monitoring services includes a computer processor and an application executing on the computer processor. The application includes a user interface. The application implements a method. The method includes sampling data for a subject over a defined time period and calculating a normative value for the defined time period based on the sampled data. The method also includes monitoring incoming data for the subject, comparing a monitored value for the incoming data to the normative value, and generating a responsive action when the monitored value deviates from the normative value.

An exemplary computer program product for providing intelligent monitoring services includes a storage medium encoded with machine-readable computer program code, which when executed by a computer, causes the computer to implement a method. The method includes sampling data for a subject over a defined time period and calculating a normative value for the defined time period based on the sampled data. The method also includes monitoring incoming data for the subject, comparing a monitored value for the incoming data to the normative value, and generating a responsive action when the monitored value deviates from the normative value.

Other systems, methods, and/or computer program products according to exemplary embodiments will be or become apparent to one with skill in the art upon review of the following drawings and detailed description. It is intended that all such additional systems, methods, and/or computer program products be included within this description, be within the scope of the exemplary embodiments, and be protected by the accompanying claims.

BRIEF DESCRIPTION OF DRAWINGS

Referring now to the drawings wherein like elements are numbered alike in the several FIGURES.

DETAILED DESCRIPTION OF EXEMPLARY EMBODIMENTS

Exemplary embodiments include providing intelligent monitoring services. The intelligent monitoring services enable analysis of large sets of data covering a large number of data partitions to score emerging changes from the statistical norm. For a monitoring system with a large number of recorded metrics, the intelligent monitoring services provide an automated way of evaluating the metric measurements when a human cannot visually process the large numbers of metrics displayed graphically The intelligent monitoring services may be employed in a system that provides notification of changes in a non-constant metric, e.g., where the item being monitored is subject to constant and varied changes. Examples of a non-constant metric may include measurements taken on the performance of a computer processing unit (CPU), blood pressure data, wind speed data, etc. The intelligent monitoring services uses values taken over a period of time to determine a mathematical norm. The mathematical norm may be derived using techniques, such as a trend line (polynomial) or other methods. Checks of the current value taken may be compared against the trend (i.e., normative value) to determine if this current value is a normal variation or something abnormal that should generate a notification. The intelligent monitoring services obviate the need to pre-define a normative value. Rather, the services enable the monitored data itself determine the normative value.

In one exemplary embodiment, a relational database and set theory are used to parallel calculation of trend line components. Trend lines for a large number of metric groups can be efficiently calculated as well as their first and second derivatives. By forward loading the "current" value and evaluating the corresponding change to the trend line derivatives, the dissimilar metrics can be evaluated together to rapidly identify metrics that are changing from a norm. These features are described further herein.

Figure 1:
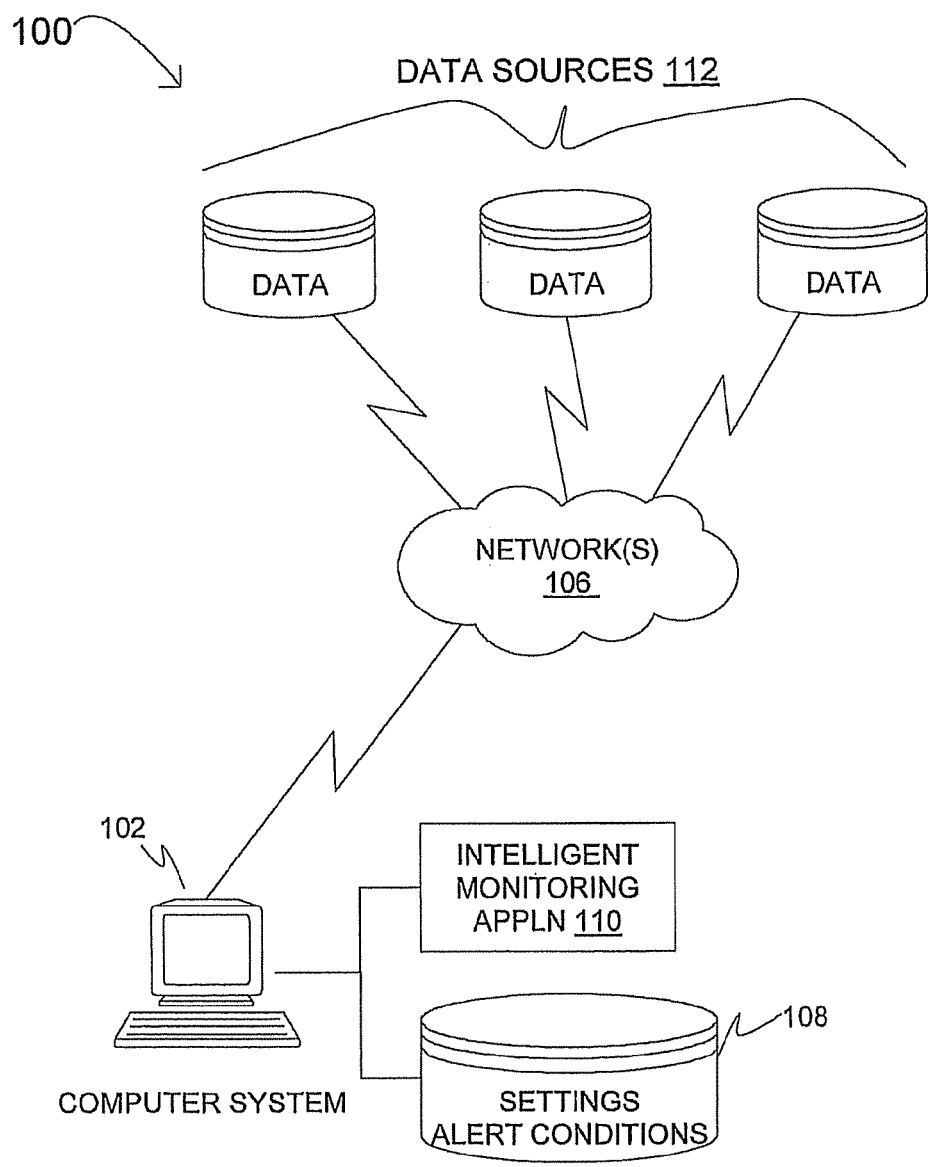
FIG. 1 is a block diagram of a system upon which intelligent monitoring services may be implemented in exemplary embodiments.

Turning now to FIG. 1, a system upon which intelligent monitoring services may be implemented in exemplary embodiments will now be described. The system of FIG. 1 includes a computer system 102 in communication with data sources 112 over one or more network(s) 106. In an exemplary embodiment, the computer system 102 is implemented by an entity tasked with data monitoring and analysis for a number of data sources, such as data sources 112. For example, data subject to monitoring may be biometric data for patients in a health care environment, such as heart rate, blood pressure, and body temperature. Another example of data subject to monitoring may include meteorological data such as wind speed, air temperature, and atmospheric pressure. A further example may include computer or network performance data, such as processing speed, bandwidth capacity, and latency.

Computer system 102 may be implemented using one or more servers operating in response to a computer program stored in a storage medium accessible by the server(s). The computer system 102 may operate as a network server (e.g., a web server) to communicate with data sources 112 or other desired network entities. Alternatively, the computer system 102 may be implemented as a general-purpose computer (e.g., desktop, laptop, etc.). The computer system 102 handles sending and receiving information to and from data sources 112 and can perform associated tasks.

The computer system 102 executes one or more applications in support of the intelligent monitoring services. Such applications may include, e.g., a database management system (not shown) that coordinates access to various data repositories and manages the data obtained therefrom. In an exemplary embodiment, the computer system 102 also executes one or more applications for facilitating the intelligent monitoring services. These one or more applications are collectively referred to herein as an intelligent monitoring application 110.

In exemplary embodiments, computer system 102 is in communication with a storage device 108. Storage device 108 may be implemented using memory contained in the computer system 102 or it may be a separate physical or virtual or logical device. As shown in FIG. 1, the storage device 108 is in direct communication with the computer system 102 (via, e.g., cabling). However, other network implementations may be utilized. For example, storage device 108 may be logically addressable as a consolidated data source across a distributed environment that includes one or more networks 106. Information stored in the storage device 108 may be retrieved and manipulated via the computer system 102. In an exemplary embodiment, storage device 108 may be configured to store data using relational databases through database management system structured query language (SQL) queries. Storage device 108 stores data monitoring settings, configurable alert conditions, and other related information, as described further herein.

As indicated above, the computer system 102 is also in communication with data sources 112. The data sources 112 may include independent sources of information stored in separately located data repositories that are accessed by the intelligent monitoring services. Data sources 112 may be may be implemented using memory contained in physical or virtual or logical devices that are distinct from the storage device 108. For example, data sources 112 may each be logically addressable as a consolidated data source across a distributed environment that includes one or more networks 106. Information stored in the data sources 112 may be retrieved and manipulated via the computer system 102. Operators of computer system 102 request and receive information provided via the intelligent monitoring services.

Network(s) 106 may include any type of known networks including, but not limited to, a wide area network (WAN), a local area network (LAN), a global network (e.g. Internet), a virtual private network (VPN), and an intranet. The network(s) 106 may be implemented using wireless networks (WiFi, satellite, cellular, etc.) or any kind of physical network implementation known in the art.

Figure 2:
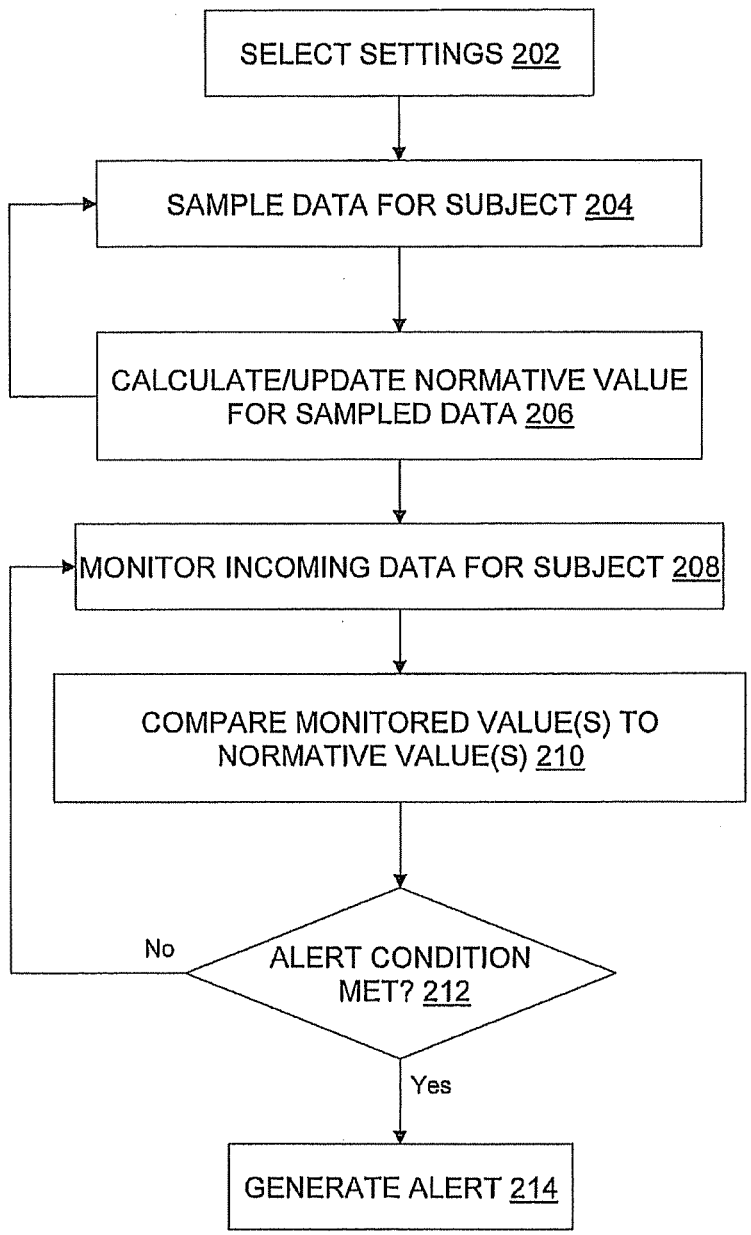
FIG. 2 is a flow diagram describing a process for implementing intelligent monitoring services in exemplary embodiments.
Figure 3:
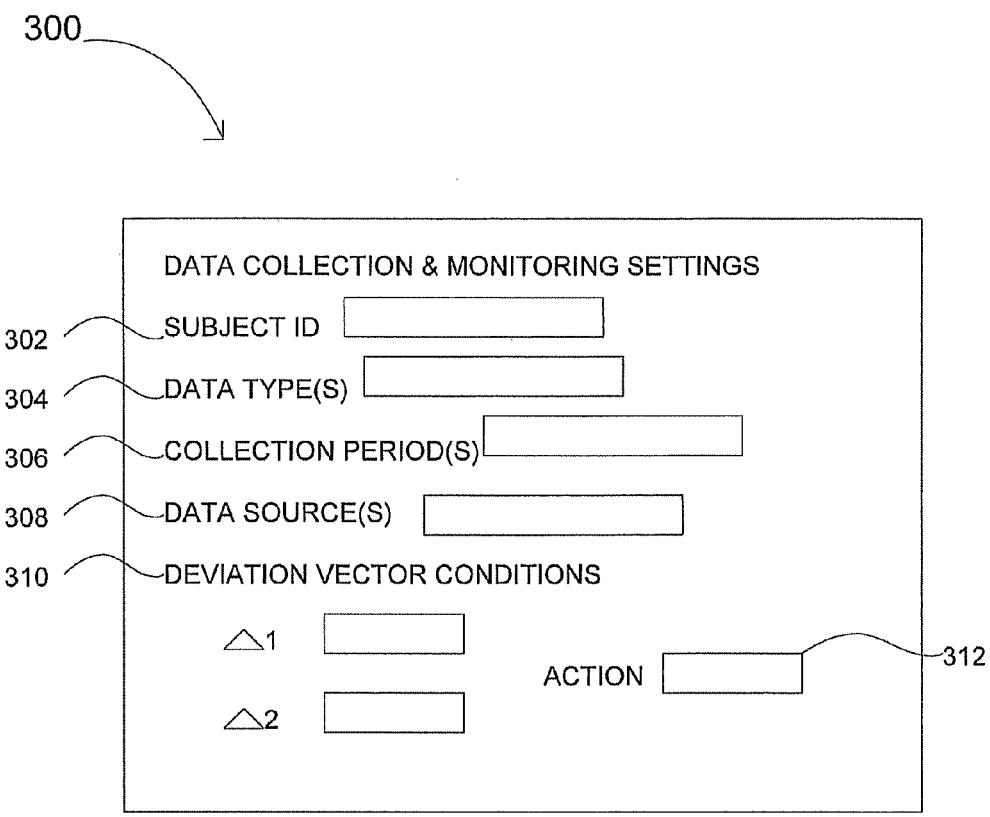
FIG. 3 is a user interface screen provided by the intelligent monitoring services in exemplary embodiments.

FIG. 2 is a flow diagram describing an exemplary process for implementing the intelligent monitoring services, and FIG. 3 depicts a user interface screen 300 of the intelligent monitoring application 110. Turning now to FIGS. 2 and 3, an exemplary process and user interface for implementing the intelligent monitoring services will now be described.

The intelligent monitoring application 110 user interface screen 300 is presented to a user of the services, e.g., via the computer system 102. The user is prompted via the user interface screen 300 to enter various settings at step 202. As shown in FIG. 3, e.g., settings may include a subject identification field 302, a data type(s) field 304, a collection period(s) field 306, data source(s) field 308, and a deviation vector conditions fields 310 and action field 312 for defining conditions, which when met, trigger a responsive action. In an exemplary embodiment, the subject identification field 302 is a unique identifier for the target or subject to be monitored. For example, the subject may be a patient whose biometric data are captured/monitored through a medical device. Alternatively, the subject may be a computer processor unit (CPU) from which performance data is captured/monitored. It will be understood that the subject data to be monitored may include any type of data in which normative values change (i.e., are non-constant) over time. The data type(s) field 304 represents one or more types of data to be collected (e.g., in a medical environment, the types of data may include heart rate, blood pressure, body temperature, etc.). The collection period(s) field 306 represents one or more time durations for which the data is to be collected (e.g., a date or time range). The data source(s) field 308 indicates the identity of the data sources (e.g., sources 112) that are subject to the data collection (e.g., a heart rate monitor coupled to a patient). The deviation vector condition fields 310 reflects conditions defined for one or more fields 310, which when met cause a corresponding responsive action (via action field 312) to be implemented. A first condition (e.g., deviation vector condition for a first derivative) may be defined that sets a threshold deviation value as a trigger point. The threshold deviation value may be represented as a percentage of deviation from the normative value. A second condition (e.g., deviation vector condition for a second derivative) may be defined that sets a threshold rate of deviation value as a trigger point (e.g., a deviation of the first condition over a defined time period). When combined conditions (first and second conditions) are met, a responsive action may be taken that is different than a responsive action otherwise taken when, e.g., only the first condition is met. Examples of these concepts are provided further herein. The deviation threshold value may include ±percentage value. In this embodiment, the deviation threshold value is met when the monitored value deviates from the normative value by the ±percentage value. Moreover, using both vector values, the responsive action may be based upon a relative change over period of time, for example ±20% of the normal for more than two minutes.

Once these settings are provided, the intelligent monitoring application 110 samples data for the identified subject based upon the criteria entered in the fields 302-308 of the user interface screen 300 at step 204. The data may be sampled across multiple data sources and/or across multiple data partitions for a data source. These parameters may be defined via the data type field 304 and/or the data source(s) field 308. At step 206, the intelligent monitoring application 110 uses the sampled data from step 204, in conjunction with a set of rules and instructions to calculate a normative value for the sampled data. As shown in FIG. 2, this normative value is dynamically updated in response to ongoing or periodic data sampling (as illustrated by the arrow looping from step 206 back to step 204). In one exemplary embodiment, a trend line polynomial may be used to calculate the normative value. A relational database (e.g., stored in storage device 108) may be used to generate trend line equations for the sampled data through parallel operations. This provides a simple parallel processing methodology that allows the computations to be conducted in real-time. The first and second derivatives of these trend line functions may be calculated in the same sequence of SQL operations. The results, when algorithmically compared, provide scoring for each metric for normative, current deviation from norm, and rate of deviation, respectively. The use of first and second derivatives for scoring, as opposed to only the first derivative, provides a vector versus scalar scoring of the most recent measured data points. The first derivative scores the amplitude of the change while the second derivative scores the amplitude change in relation to time. The use of the vector scoring allows for a greater level of discrimination in asserting alert conditions.

The above methodology will now be described with respect to example data for purposes of illustration. Suppose a patient's normal pulse rate oscillates in the range of 75-82 bests per minute (bpm). When viewing a data point showing a pulse rate at 130 bpm, the deviation is substantial and depending upon rules may assert an a responsive action (e.g., an alarm). The deviation is measured by scoring the first derivate. The second aspect of the scoring is evaluating whether the pulse increased from 82 to 130 instantly (in a matter of seconds) versus over an extended period of time, perhaps 5 minutes. The instant rise may likely indicate a radical change in the patient's condition which may generate one level of response (an emergency alert to the nurse's station), whereas a slow rise in bpm may generate another responsive action (e.g., sounding a beeping mechanism on the heart rate machine).

Turning back to FIG. 2, at step 208, the intelligent monitoring application 110 monitors incoming data from the subject to identify a current, real-time monitored value. The current monitored value is compared with the normative value at step 210. As indicated above, the normative value may be continually updated and reflects a non-static variable produced from ongoing data sampling over time. At step 212, the intelligent monitoring application 110 determines if an alert condition has been met based upon the comparison performed in step 210. If so, the intelligent monitoring application 110 generates an alert at step 214. The alert may be displayed or otherwise presented via the computer system 102 or other device configured by the entity implementing the intelligent monitoring services.

If, however, the alert condition is not met at step 212, the process returns to step 208 and the intelligent monitoring application 110 continues to monitor the incoming data.

As described above, the exemplary embodiments can be embodied in the form of computer-implemented processes and apparatuses for practicing those processes. The exemplary embodiments can also be embodied in the form of computer program code containing instructions embodied in tangible media, such as floppy diskettes, CD ROMs, hard drives, or any other computer-readable storage medium, wherein, when the computer program code is loaded into and executed by a computer, the computer becomes an apparatus for practicing the invention. The exemplary embodiments can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes an apparatus for practicing the exemplary embodiments. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims.

What is claimed is:

1. A method for providing intelligent monitoring services, comprising:
   receiving a deviation threshold value via a deviation vector conditions field of a user interface of an application;
   receiving a rate of deviation threshold value via another deviation vector conditions field of the user interface of the application;
   receiving a responsive action via an action field of the user interface of the application;
   sampling data for a subject over a defined time period, the data sampled via a computer processor;
   calculating, via the application executing on the computer processor, a normative value for the defined time period based on the data;
   monitoring, via the application, incoming data for the subject;
   comparing, via the application, a monitored value for the incoming data to the normative value; and
   generating, via the application, the responsive action when the comparing of the monitored value to the normative value indicates that the deviation threshold value and rate of deviation threshold value are met.

2. The method of claim 1, further comprising: receiving data into data fields, via the user interface of the application, the data in the data fields specifying a subject identification of the subject, a type of data subject to the sampling, a time duration comprising the defined time period for sampling, and a data source from which the data is sampled;
   wherein sampling the data is performed in response to data in the data fields.

3. The method of claim 1, wherein the deviation threshold value includes:
   a ±percentage value.

4. The method of claim 1, wherein the normative value is calculated using a
   trend line polynomial equation.

5. The method of claim 1, further comprising:
sampling data for the subject over another defined time period, the data sampled via the computer processor;
recalculating, via the application, the normative value for the other defined time period to provide a recalculated normative value;
monitoring, via the application, other incoming data for the subject;
comparing, via the application, a monitored value for the other incoming data to the recalculated normative value; and
generating, via the application, the responsive action when the monitored value derived from the other incoming data deviates from the recalculated normative value.

6. The method of claim 1, wherein sampling the data includes
collecting data across multiple data sources.

7. A system for providing intelligent monitoring services, comprising:
a computer processor; and
an application executing on the computer processor, the application including a user interface, the application implementing a method, the method comprising:
receiving a deviation threshold value via a deviation vector conditions field of the user interface of the application;
receiving a rate of deviation threshold value via another deviation vector conditions field of the user interface of the application;
receiving a responsive action via an action field of the user interface of the application:
sampling data for a subject over a defined time period;
calculating a normative value for the defined time period based on the sampled data;
monitoring incoming data for the subject;
comparing a monitored value for the incoming data to the normative value; and
generating the responsive action when the comparing of the monitored value to the normative value indicates that the deviation threshold value and the rate of deviation threshold value are met.

8. The system of claim 7, wherein the application further implements:
receiving data into data fields, via a user interface of the application, the data in the data fields specifying a subject identification of the subject, a type of data subject to the sampling, a time duration comprising the defined time period for sampling, and a data source from which the data is sampled;
wherein sampling the data is performed in response to data in the data fields.

9. The system of claim 7, wherein the deviation threshold value includes:
a ±percentage value.

10. The system of claim 7, wherein the normative value is calculated using a trend line polynomial equation.

11. The system of claim 7, wherein the application further implements:
sampling data for the subject over another defined time period;
recalculating the normative value for the other defined time period to provide a recalculated normative value;
monitoring other incoming data for the subject;
comparing a monitored value for the other incoming data to the recalculated normative value; and
generating the responsive action when the monitored value derived from the other incoming data deviates from the recalculated normative value.

12. A computer program product for providing intelligent monitoring services, the computer program product comprising a non-transitory storage medium including machine-readable program code, which when executed by a computer processor causes the computer processor to implement a method, the method comprising:
receiving a deviation threshold value via a deviation vector conditions field of a user interface of an application;
receiving a rate of deviation threshold value via another deviation vector conditions field of the user interface of the application;
receiving a responsive action via an action field of the user interface of the application;
sampling data for a subject over a defined time period;
calculating a normative value for the defined time period based on the sampled data;
monitoring incoming data for the subject;
comparing a monitored value for the incoming data to the normative value; and
generating the responsive action when the comparing of the monitored value to the normative value indicates that the deviation threshold value and the rate of deviation threshold value are met.

13. The computer program product of claim 12, wherein the program code further implements:
entering data into data fields, via the user interface of the application, the data in the data fields specifying a subject identification of the subject, a type of data subject to the sampling, a time duration comprising the defined time period for sampling, and a data source from which the data is sampled;
wherein sampling the data is performed in response to data in the data fields.

14. The computer program product of claim 12, wherein the deviation threshold value includes:
a ±percentage value.

15. The computer program product of claim 12, wherein the normative value is calculated using a trend line polynomial equation.

16. The computer program product of claim 12, wherein the program code further implements:
sampling data for the subject over another defined time period;
recalculating the normative value for the other defined time period to provide a recalculated normative value;
monitoring other incoming data for the subject;
comparing a monitored value for the other incoming data to the recalculated normative value; and
generating the responsive action when the monitored value derived from the other incoming data deviates from the recalculated normative value.

17. The computer program product of claim 12, wherein sampling the data includes collecting data across multiple data sources.

* * * * *